US010709416B2

(12) United States Patent
Feltovich et al.

(10) Patent No.: US 10,709,416 B2
(45) Date of Patent: Jul. 14, 2020

(54) OBSTETRICAL IMAGING AT THE POINT OF CARE FOR UNTRAINED OR MINIMALLY TRAINED OPERATORS

(71) Applicant: Wisconsin Alumni Research Foundation, Madison, WI (US)

(72) Inventors: Helen Feltovich, Park City, UT (US); Timothy Hall, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 369 days.

(21) Appl. No.: 15/066,290

(22) Filed: Mar. 10, 2016

(65) Prior Publication Data

US 2017/0000453 A1 Jan. 5, 2017

Related U.S. Application Data

(60) Provisional application No. 62/187,079, filed on Jun. 30, 2015.

(51) Int. Cl.
*A61B 8/08* (2006.01)
*A61B 8/00* (2006.01)

(52) U.S. Cl.
CPC .............. *A61B 8/0866* (2013.01); *A61B 8/08* (2013.01); *A61B 8/0833* (2013.01);
(Continued)

(58) Field of Classification Search
CPC ....... A61B 8/5292; A61B 8/5215; A61B 8/52; A61B 8/483; A61B 8/48; A61B 8/467;
(Continued)

(56) References Cited

U.S. PATENT DOCUMENTS 5,795,296 A * 8/1998 Pathak ................. A61B 5/1075
600/443
6,280,387 B1 * 8/2001 Deforge .................. A61B 8/06
128/916
(Continued)

FOREIGN PATENT DOCUMENTS

CN 102151149 8/2011
JP 2002282203 A 10/2002

OTHER PUBLICATIONS

Incremental Volume Rendereing Algorithm for Interactive 3D Ultrasound Imaging by Ohbuchi et al. pub. Information Processing in Medical Imaging pp. 486-500. ISBN 978-3-540-47521-7 (Year: 1991).*

(Continued)

*Primary Examiner* — Katherine L Fernandez
*Assistant Examiner* — Michael S Kellogg
(74) *Attorney, Agent, or Firm* — Boyle Fredrickson S.C.

(57) ABSTRACT

A specialized ultrasound machine tailored for use by traditional birth attendants provides an ultrasound transducer configuration adapted to work with the traditional sweeping motion of the attendant's hands over the patient's abdomen. Automatic analysis of various obstetrical conditions is performed without the need for the user to view or interpret standard ultrasound images. This machine analysis is used to provide real-time guidance in the acquisition of data by the user greatly reducing the required operator skill.

25 Claims, 4 Drawing Sheets

(52) U.S. Cl.
CPC .......... *A61B 8/4427* (2013.01); *A61B 8/4444* (2013.01); *A61B 8/4455* (2013.01); *A61B 8/4477* (2013.01); *A61B 8/483* (2013.01); *A61B 8/5223* (2013.01)

(58) Field of Classification Search
CPC .. A61B 8/461; A61B 8/46; A61B 8/44; A61B 8/42; A61B 8/4494; A61B 8/4483; A61B 8/4455; A61B 8/4444; A61B 8/4245; A61B 8/4209; A61B 8/0866
See application file for complete search history.

(56) References Cited

U.S. PATENT DOCUMENTS

| | | | | |
|---|---|---|---|---|
| 6,500,119 | B1 * | 12/2002 | West | A61B 5/0053 600/437 |
| 6,575,167 | B1 * | 6/2003 | McFadden | A61B 8/0833 128/846 |
| 2002/0133075 | A1 * | 9/2002 | Abdelhak | A61B 8/0858 600/443 |
| 2004/0019270 | A1 * | 1/2004 | Takeuchi | A61B 8/14 600/407 |
| 2005/0154303 | A1 * | 7/2005 | Walker | A61B 5/415 600/443 |
| 2006/0025690 | A1 * | 2/2006 | Guigne | A61B 5/6806 600/459 |
| 2006/0100521 | A1 | 5/2006 | Takeuchi | |
| 2006/0173331 | A1 * | 8/2006 | Booton | A61B 8/00 600/445 |
| 2008/0146936 | A1 * | 6/2008 | Furia | A61B 8/00 600/459 |
| 2008/0177138 | A1 * | 7/2008 | Courtney | A61B 5/0062 600/109 |
| 2009/0093717 | A1 * | 4/2009 | Carneiro | A61B 5/1075 600/443 |
| 2011/0079082 | A1 * | 4/2011 | Yoo | G01S 7/52065 73/632 |
| 2011/0196235 | A1 * | 8/2011 | Dunbar | A61B 8/00 600/437 |
| 2011/0224551 | A1 * | 9/2011 | Barnard | A61B 8/08 600/445 |
| 2012/0078110 | A1 * | 3/2012 | Yamamoto | A61B 8/42 600/459 |
| 2012/0209121 | A1 * | 8/2012 | Boudier | A61B 8/4455 600/459 |
| 2013/0002843 | A1 * | 1/2013 | Horiike | A61B 5/0066 348/65 |
| 2013/0226001 | A1 | 8/2013 | Steen et al. | |
| 2013/0261465 | A1 | 10/2013 | Nakamura et al. | |
| 2013/0263438 | A1 * | 10/2013 | Burns | A61B 8/44 29/592.1 |
| 2014/0066769 | A1 * | 3/2014 | Wang | A61B 8/4494 600/443 |
| 2014/0153358 | A1 * | 6/2014 | Balakrishnan | G01S 7/52074 367/7 |
| 2014/0189560 | A1 | 7/2014 | Caspi | |

OTHER PUBLICATIONS

International Search Report & Written Opinion for Application No. PCT/US2016/039497; filed Jun. 27, 2016.

* cited by examiner

OBSTETRICAL IMAGING AT THE POINT OF CARE FOR UNTRAINED OR MINIMALLY TRAINED OPERATORS

CROSS REFERENCE TO RELATED APPLICATION

This application claims the benefit of U.S. provisional application 62/187,079 filed Jun. 30, 2015, and hereby incorporated by reference in its entirety.

STATEMENT REGARDING FEDERALLY SPONSORED RESEARCH OR DEVELOPMENT

BACKGROUND OF THE INVENTION

The present invention relates to medical imaging equipment and in particular to ultrasound equipment adapted for use by operators untrained in conventional imaging.

Despite significant global effort mothers and newborns continue to die from preventable causes. One common example is hemorrhage from poor uterine tone due to obstructed labor (from fetal malpresentation, multiple gestation, etc.) or placenta over the cervix (placenta previa) A quick ultrasound exam establishes fetal presentation, number, size (gestational age), and placental location. Therefore, in high-income countries where the standard of pregnancy care includes at least one ultrasound exam, these potentially life-threatening situations are rarely a surprise.

In low- and middle-income countries, however, where both ultrasound systems and personnel trained in image acquisition and interpretation are a rarity, these conditions can be extremely dangerous. In such places, a simple diagnostic tool that is easily operated by the untrained user at the point of care could be literally life-saving. An example of a low-income country is Bangladesh, where most deliveries in rural areas (~2/3) are attended by unskilled traditional birth attendants (TBAs, called Dais), and most of the others by (typically minimally skilled) nurses or midwives. Even in areas where skilled care is available, Dais are often preferred by rural women because they reside in the community, and are part of its social and cultural matrix. For this reason in the 1970s-90s the World Health Organization focused on training TBAs, but this practice has been abandoned because ultimately it had no effect on maternal death and minimal effect on peri/neonatal death. Reasons include the lack of imaging equipment; even the best trained providers cannot look inside the uterus without an appropriate device.

Technology that allows users untrained in ultrasound diagnostics to make point-of-care decisions would, in fact, be useful any place in the world where there is not immediate access to an ultrasound system and provider trained in its use; examples of this in the U.S.A. include places where rapid decisions are needed to provide optimal care, such as the site of an motor vehicle accident where emergency medical technicians must evaluate a pregnant woman, or a rural labor and delivery unit where nurses, but not radiology personnel, are in house.

SUMMARY OF THE INVENTION

The present invention provides a medical imaging machine that is ultrasound-based and specifically tailored to unskilled users and their familiar practices and capabilities. The present invention may employ an ultrasound transducer redesigned to work better with the sweeping motion commonly used by obstetrical providers for assessing pain, fundal height, and fetal position. In addition, real-time guidance can be provided with respect to manipulation of the ultrasound transducer to obtain the necessary data. A conventional display of an ultrasound image, which requires skill and experience to interpret, is eliminated in favor of machine analysis providing an output in abbreviated or cartoon form.

Specifically, then, the present invention provides, in one embodiment, an ultrasound machine having an ultrasound transducer communicating with an ultrasound processor. The ultrasound transducer has a transducer bar having an upper surface receivable against a palm of a hand placed there against to extend across a lateral axis of the palm and a hand retention element extendable upward from the transducer bar over the back of the hand to retain the transducer bar against the palm. A set of independently excitable transducer elements are displaced laterally within the transducer bar and exposed for ultrasonic transmission and reception at a lower surface of the transducer bar opposite the upper surface.

The ultrasound processor includes transducer interface circuitry communicating with the independently excitable transducer elements for acquisition of a volume set of ultrasound echo signals, a display and an electronic processor receiving the volume set of ultrasound echo signals. The electronic processor executes a stored program to identify within the volume set of ultrasound echo signals indications of conditions selected from the group of: (i) placenta over cervix; (ii) fetus in non-head down presentation; (iii) multiple gestation; (iv) gestational age; (v) and fetal size; and to output at least one condition on the display.

It is thus a feature of at least one embodiment of the invention to provide an ultrasound machine that accommodates the practice of existing providers who are untrained in imaging (or even obstetrics) rather than requiring the traditional birth attendants or point-of-care healthcare workers (such as emergency medical technicians) to conform to the requirements of complex ultrasound technology. By offering limited functionality related to obstetrical care, the complexity of ultrasound diagnosis can be largely managed automatically. By adapting the transducer to be compatible with current practices of the attending assistant, training time is substantially reduced and acceptance of the equipment into the practice of those actually available to provide healthcare is greatly increased.

The hand retention element and transducer bar may be substantially symmetric across the lateral axis to receive either the left or right hand.

It is thus a feature of at least one embodiment of the invention to provide a transducer that may be employed in a familiar hand position with palm toward the patient when used in either the left or right hand, allowing for complete data acquisition The ultrasound producer may include indicia indicating preferred movement direction.

It is thus a feature of at least one embodiment of the invention to assist in the automatic identification of the orientation of the acquired data through enforcement of a single orientation of the transducer on the hand, left or right.

The ultrasound machine may output the measured condition independent of a representation of an image of the volume set of ultrasonic echo signals.

It is thus a feature of at least one embodiment of the invention to eliminate the need for interpreting an image to obtain the needed clinical information.

In some embodiments, the invention may output the measured condition without outputting a representation of an image of the volume set of ultrasonic echo signals and in a way that is free from information identifying gender.

It is thus a feature of at least one embodiment of the invention to avoid enabling gender selection.

The electronic processor may further output on the display indications guiding movement of the ultrasonic transducer to obtain the volume set of ultrasonic echo signals.

It is thus a feature of at least one embodiment of the invention to provide a system that may be used with little or no training by providing real-time user instructions directly into the display.

The indications guiding movement of the ultrasonic transducer may be based on concurrent, analysis of the received ultrasound signals by the electronic processor, for example, as to quantity and location and/or based on real-time analysis of fetal structure. In this latter case, the indications guiding movement of the ultrasound transducer may be based on identified fetal structure that must be measured for identification of the at least one condition.

It is thus a feature of at least one embodiment of the invention to provide guidance in using the ultrasound machine that is responsive to the ongoing data collection process and thus that provides continued guidance to the user. It is a thither feature of this embodiment to inform the guidance provided by the user, on a real-time basis, using the same features that allow for automatic ultrasound analysis, that is, to allow concurrent automatic analysis of the data to adjust the user's actions toward the goal of improving the intended measurements of the automatic analysis.

The indications guiding movement of the ultrasound transducer provide a representation of the ultrasonic transducer positioned, on a representation of the mother's abdomen.

It is thus a feature of at least one embodiment of the invention to provide a simple, intuitive, and largely language-free guidance to the user.

These particular objects and advantages may apply to only some embodiments falling within the claims and thus do not define the scope of the invention.

DETAILED DESCRIPTION OF THE PREFERRED EMBODIMENT

Figure 1:
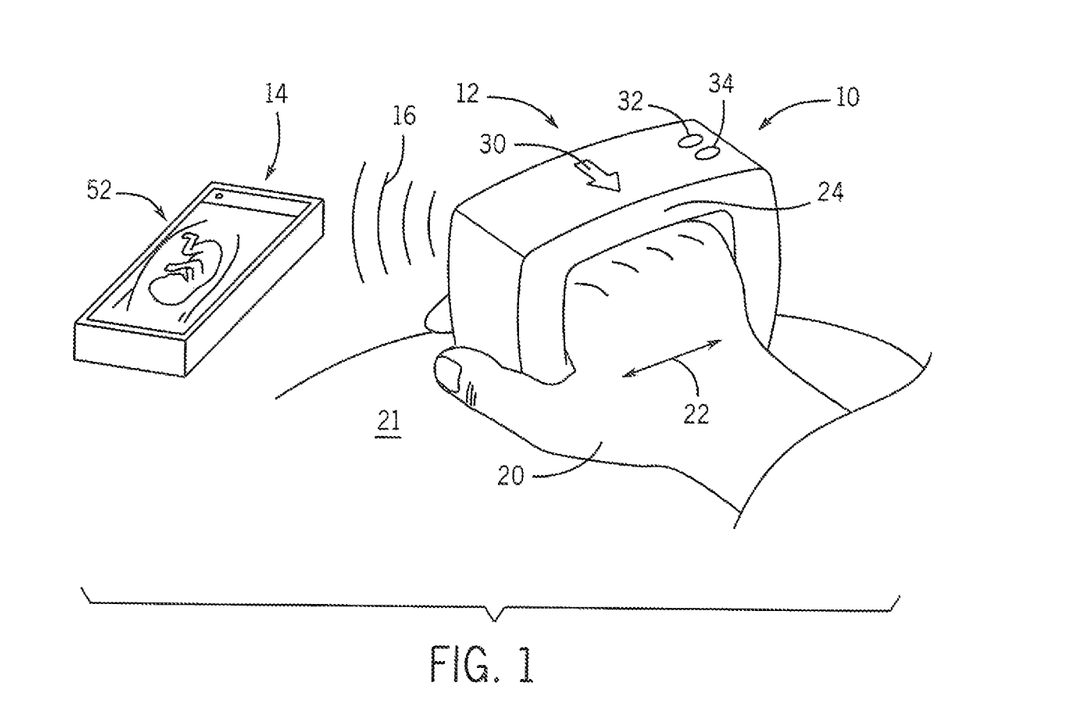
FIG. 1 is a perspective view of the ultrasound machine of the present invention showing the transducer design as is adapted for better compatibility with traditional obstetrical practice, and further showing a remote display unit communicating with this transducer.

Referring now to FIG. 1, an ultrasound system 10 of the present invention may include an ultrasound transducer 12 for acquiring ultrasound echo data and communicating that ultrasound data with a display unit 14 for the display of information related to acquired ultrasound data. As shown, the transducer 12 and display unit 14 are separate so as to aid in the viewing of the display unit 14 during scanning of the transducer 12: however, it is contemplated that these two elements can be integrated into a single device. When separate, the transducer 12 may communicate with the display unit 14, for example, wirelessly by radio, ultrasound, or optical signals 16 or by means of a flexible electrical conductor.

Figure 2:
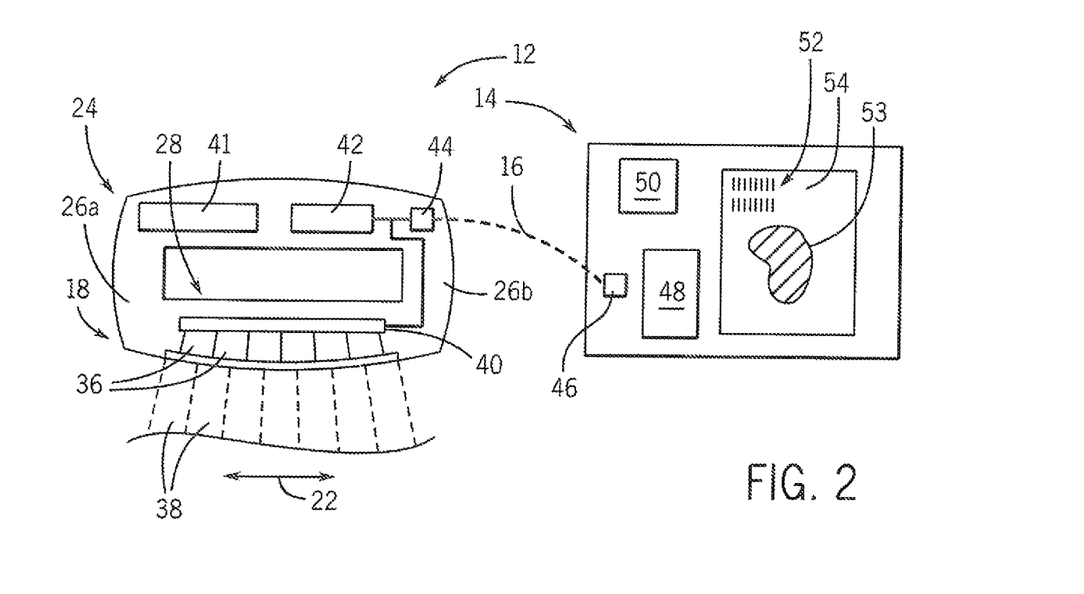
FIG. 2 is a block diagram of the transducer and display unit of FIG. 1 showing positioning of the ultrasound transducer elements and showing a first and second electronic computer for processing ultrasound data in the transducer and generating a display in the remote display unit.

Referring now to FIGS. 1 and 2, the transducer 12 may include a transducer bar 18 receivable against a palm of the user's hand 20 to extend generally along a lateral axis 22 with respect to the hand 20 across the width of the hand 20 over the palm. A hand retention bar 24 may be spaced above the transducer bar 18, generally parallel to the transducer bar 18, as supported by left and right side pillars 26a and 26b. In this way, the hand retention bar 24 may fit against the back of the user's hand 20 when the user's hand 20 is placed within an opening 28 between the pillars 26a, 26b and between the upper surface of the transducer bar 18 and the lower surface of the hand retention bar 24. The hand retention bar 24 and the pillars 26a and 26b allow the transducer 12 to be manipulated with a light grip by the user's hand 20 in a manner that orients the user's hand in a traditional orientation for a sweeping of the abdomen 21 of a patient. The pillars 26a and 26b on the underside of hand retention bar 24 may be lightly padded to help the user retain possession of the transducer 12 during use and to prevent the need for a tight grip on the transducer bar 18 in order to control lateral and vertical motion of the transducer 12.

As shown in FIG. 1, an upper surface of the hand retention bar 24 may provide a directional indicia 30 indicating a preferred sweep direction of the transducer 12 generally perpendicular to the lateral axis 22. The transducer 12 is generally symmetrical across a central plane perpendicular to the lateral axis 22 to be equally received by the user's left or right hand. The indicia 30 helps preserve the consistent orientation of the transducer 12 when the user switches hands.

An upper surface of the hand retention bar 24 may also include control features such as an indicator light 32 indicating activation and proper functioning of the ultrasound system 10 in communication with the display unit 14, and an activation button 34 that may control the application of power to internal electronics of the transducer 12 in the manner of a conventional on-off switch.

Referring still to FIG. 2, positioned within the transducer bar 18 are a set of independent transducer elements 36 each capable of emitting ultrasonic acoustic waves into tissue in contact with the underside of the transducer bar 18 and of receiving and detecting echo signals from those emitted ultrasonic acoustic waves for the generation of ultrasonic data. The transducer elements 36 are independently controllable so as to provide separate diverging ultrasonic beams 38 that may be controlled in amplitude and phase for beamforming and other known techniques and are spaced along the lateral axis 22.

The transducer elements 36 may communicate with driver circuitry 40 of a type known in the art for providing appropriate voltage signals for driving the transducer elements 36 and for detecting voltage signals representing received echo signals from the transducer elements 36.

An internal cavity in the transducer bar 18 holding the transducer elements 36 and the driver circuitry 40 may communicate, for example, through an interconnected cavity in pillar 26a with additional circuitry held in a corresponding cavity of the hand retention bar 24. This latter cavity may include a battery 41 and processing circuitry 42 and communication interface 44, the latter two elements powered by the battery 41. As is understood in the art, the processing circuitry 42 may be an electronic computer having nonvolatile memory for holding a stored program as will be described below. The communication interface 44 may be a conductor driver or a wireless transceiver operating to produce the signal 65 discussed above.

Referring still to FIG. 2, communication interface 44 may communicate the corresponding communication interface 46 in the display unit 14. Like the transducer 12, the display unit 14 may include a battery 48 providing power to the communication interface 44 as well as power to processing circuitry 50 and display screen 52 for displaying image data 53 and/or text and numeric data 54. As with processing circuitry 42, processing circuitry 50 may include an electronic computer holding a stored program held in computer memory for controlling other elements of the display unit 14, in one embodiment, the display unit 14 may be implemented through the use of a smart phone tablet or the like.

Figure 3:
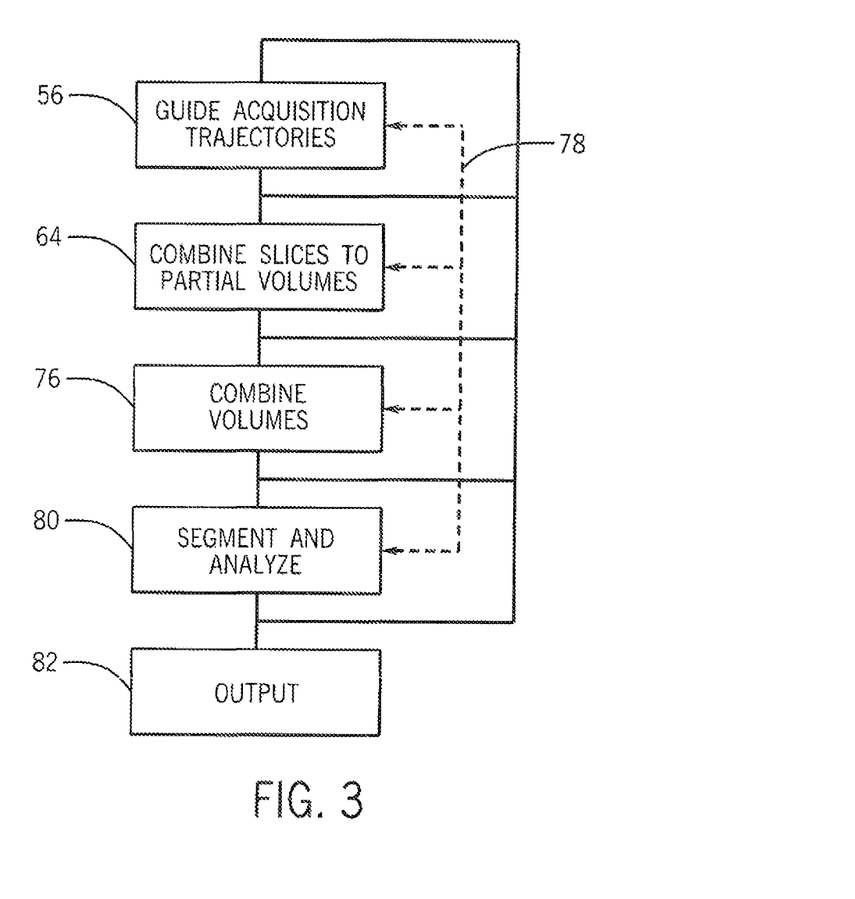
FIG. 3 is a flowchart showing a program executed jointly or individually by the computers of FIG. 2 in implementing the present invention.

Referring now to FIG. 3, in operation, the user may activate the display unit 14 and transducer 12, for example, by conventional switches on each, to receive, as indicated by process block 56, ultrasound acquisition instructions to begin an examination. Processing circuitry 42 within the transducer 12 may automatically detect contact of the transducer 12 with the patient so that the operator is not concerned with control of the ultrasound system 10 after activation and before measurements have been reported.

Figure 4:
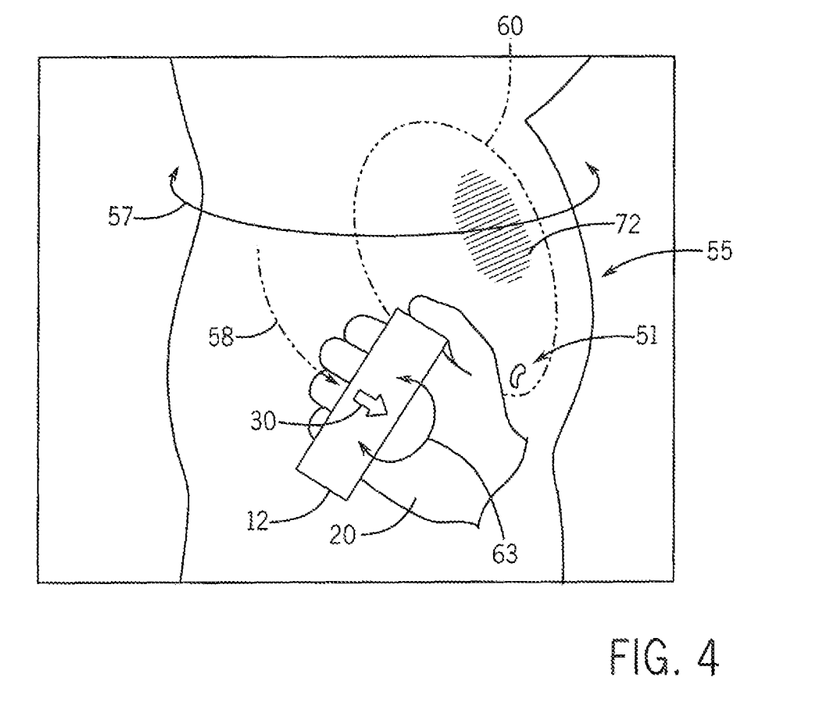
FIG. 4 is a representation of a first display provided by the display unit of FIG. 1 guiding movement of the ultrasound transducer by the operator according to real-time measurements and analysis of received ultrasound signals.

Referring now to FIG. 4, the instructions for acquiring ultrasound data may be provided to the user during the scanning process. Preferably this is done by depicting on the screen 52 a modeled image 55 of the patient's abdomen, represented internally in three dimensions, so that a two-dimensional image projection can be displayed in various rotations as shown by rotational arrow 57 to show the left and right side of the abdomen for better indicating a range of desired scanning trajectory. Superimposed on this modeled image 55 is a representation of the hand 20 of the operator placed in the transducer 12, the latter depicting the indicia 30. The representation of the hand 20 may be placed at the end of a desired sweeping trajectory 58 or may be animated to move along the desired sweeping trajectory 58. The modeled image 55 may include a phantom outline of a cartoon fetus 60 to provide additional visual reference although it should be emphasized that the model of the patient's abdomen and the phantom outline of the fetus 60 are preferably cartoons and not derived from actual ultrasound data.

Figure 6:
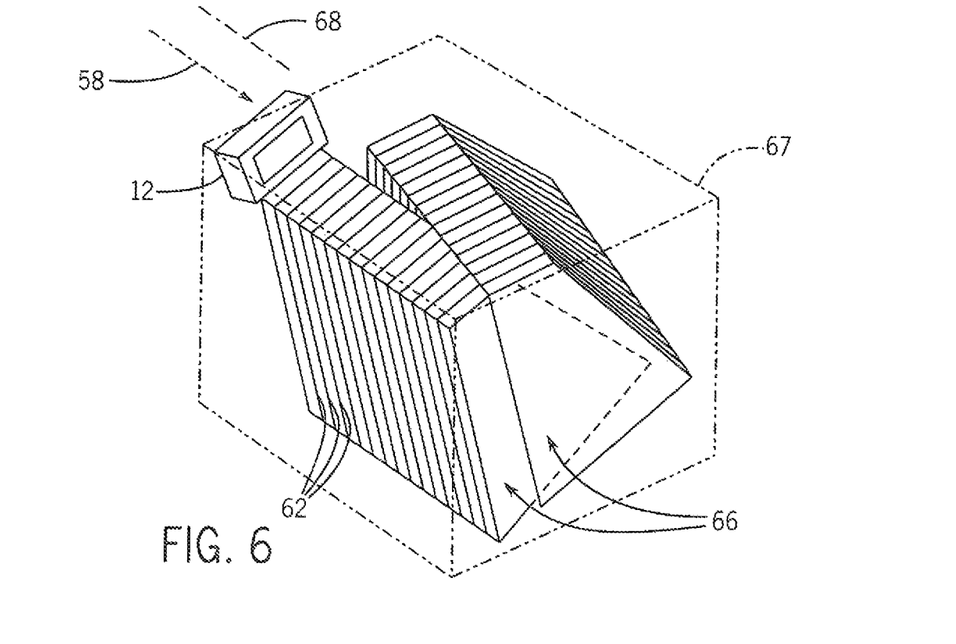
FIG. 6 is a perspective view of the transducer and data acquired by the transducer within a desired volumetric data set with respect to stitching data together to provide the volumetric data set.

Referring to FIGS. 3 and 6, as the transducer 12 is moved along various trajectories 58, it will obtain at each point in the trajectory 58 a fan beam slice 62 of ultrasonic echo data caused by successive excitations of the transducer elements 36 and reception of echo signals as is generally understood in the art. As indicated by process block 64, these slices may be "stitched" together into partial volumes 66 of a desired volumetric data set 67, for example, by correlating features at adjacent sides of each slice 62. At this time a superior/interior axis 68 is determined based on knowledge of the order of acquisition of the slices 62 from the user following the trajectory 58. Alternatively this superior/inferior axis 68 may be determined from anatomical landmarks extracted from the volume set that will be acquired.

At the conclusion or during each sweep collecting slices 62 of a partial volume 66, the instructions of process block 56 may be revised, for example, to show a new trajectory 58. This depiction of the trajectory 58 may include rotation of the modeled image 55 as appropriate and a changing of the image of the hand of the user as well as rotation of the orientation of the representation of the transducer 12 indicated by arrow 63. In addition, and as shown in FIG. 4, a three-dimensional shading 72 may be placed over the outline of the fetus 60 showing roughly the acquired data of each partial volume 66 to guide the user in obtaining data over the entire volumetric data set 67.

As indicated by process block 70, as additional partial volumes 66 are obtained at process block 69, those volumes are stitched together at process block 76. Again this process may make use of a correlation of adjacent partial volumes 66 and/or common anatomical references. In this latter case, for example, the border between the amniotic fluid and uterine wall provides a sharp contrast reference point for the alignment of images. This technique is described in "A three-dimensional, extended field of view ultrasound method for estimating large strain mechanical properties of the cervix during pregnancy" by Michael House, Helen Feltovich Timothy J Hall, Trevor Stack, Atur Patel, and Simona Socrate in Ultrasound Imaging. 2012 January; 34(1): 1-14, hereby incorporated by reference together with the references cited therein.

As these partial volumes 66 are collected at process block 76, instructions of process block 56 are again updated to show new trajectories 58 or repetitions of old trajectories 58 and to update the shading 72. Note that generally the shading 72 may include several intensities, for example, reflecting the desire for oversampling through multiple passes by the transducer 12.

As the partial volumes 66 are collected, analysis can begin as indicated by process block 80 in which the acquired data is segmented to identify the anatomical structure of the fetus. The early stages of the segmentation and analysis may further be used to modify the instructions for acquisition of process block 56 as indicated by dotted line 78 which may lead to more acquisition along additional trajectories 58 with different orientations. For example, in measurement of the fetal femur length or the crown-rump length of the fetus, an evolving understanding of the segmentation of volumetric data set 67 and the position of the fetus may be used to promote additional acquisition along different planes that better reveal data for this measurement.

Figure 5:
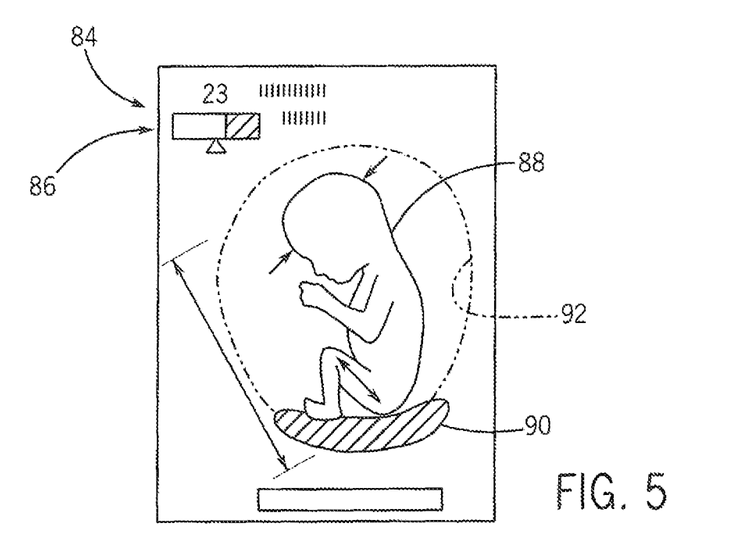
FIG. 5 is a representation of a second display provided by the display unit of FIG. 1 providing output indication of fetal conditions.

Referring now also to FIG. 5, when the completion of data acquisition of the desired volumetric data set 67 is complete, as indicated by process block 82, an output may be provided on the screen 52 of the display unit 14 providing an indication of one or more conditions relevant to the developing fetus including (i) placenta over cervix; (ii) fetus in non-head down presentation; (iii) multiple gestation; (iv) gestational age; and (v) fetal size. As is generally understood in the art, the placenta over the cervix (placenta previa) occurs when the placenta partially or totally covers the opening in the cervix which can cause bleeding or infection from obstructed labor. The fetus in the non-head down presentation (fetal malpresentation) refers to any position of the fetus other than a vertex presentation with the top of the head closest to the pelvic inlet of the birth canal such as can present difficulties in labor. Multiple gestation, for example, indicates the presence of twins or the like. Gestational age is the amount of time since conception and fetal size may be measured in a variety of ways including head size, femur size, and crown-to rump-length.

Desirably, this information is communicated either quantitatively as a number 84, or is a quantitative graphic, for example, a marker arrow showing the desired value and position within a bar 86 that establishes both a range of possible values and indicates sub-ranges associated with desired values. The meaning of each measurement, for example, measures of fetal size such as head size or femur length, may be diagrammically illustrated on a cartoon 88 of the fetus. Preferably no image derived from the ultrasound data that is collected will be displayed, to prevent attempts to diagnose with the use of the image; however, thumbnail images may be provided in a form that doesn't allow for gender identification.

When the output value is described against the range, for example, in a quantitative graphic, the range or sub-ranges may be adjusted according to other measured conditions, for example, gestational age. In this way, for example, the values may be provided in the context of desired values for a given gestational age. With respect to the conditions (i)-(iii), the cartoon 88 may be altered to illustrate those conditions, for example, by adding a cartoon 90 of the placenta for (i), inverting the image of the cartoon 88 within a cartoon perimeter 92 of the uterus for (ii). Or adding a second fetal cartoon 88 in the case of multiple gestations of condition (iii).

Figure 7:
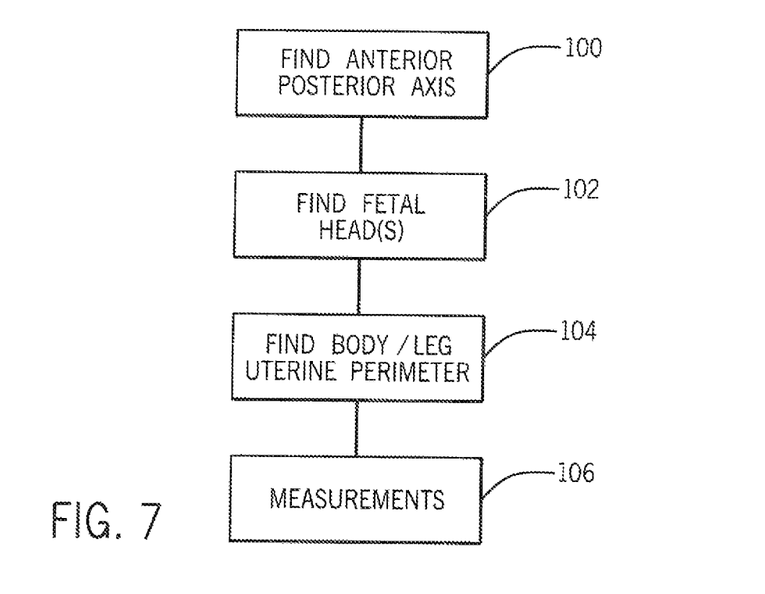
FIG. 7 is a flowchart of a segmentation procedure used by the present invention.

Referring now to FIG. 7, the process of segmentation and analysis of FIG. 3 is desirably performed automatically by segmentation and analysis programs that eliminate the need for the user to have acquired skills in reading ultrasound images. Accuracy in this process is enabled by the constrained use of the ultrasound system 10 for detecting specific conditions. The automatic segmentation analysis problem may be treated as an "ordered detection problem" in which more easily identified anatomical structures are identified first and then these structures are used as reference points to locate subsequent harder to identify structures. Thus, the approach provides a multi-resolution approach that computes the likelihood that a structure is in a particular location given the structures already identified and their relative locations.

As indicated by process block 100, the superior/inferior axis 68 shown in FIG. 6 that will be used for the analysis process is first identified either as discussed above or through a general analysis of the volumetric data for anatomical features such as pelvic bone structures and the like.

At process block 102, fetal head structure is identified, for example, by correlating against a model of the fetal head at various sizes that captures the bright reflection of the skull bone against the dark shadow of surrounding amniotic fluid, the generally spherical shape of the skull, and the expected ultrasonic characteristics of the brain tissue. Various fetal head sizes may be applied and at this point multiple heads may be identified for the purposes of identifying condition (iii) of multiple gestations. For each identified head, per process block 102, body structure may be identified per process block 104 as a tissue mass extending from an identified head by an expected distance and volume based on head diameter. The portion of the identified fetal body structure may then be analyzed to find an appropriate length femur structure consistent with the head size and location in the body structure according to empirically established zones within the body structure.

Measurement of the head size, femur length and crown-rump length may then be performed for condition (v). At this point the relationship between the head and the body structure and the known superior/inferior axis 68 developed at process block 100 will provide for an indication of condition (ii) of the fetal in the non-head down presentation. The known superior/inferior axis 68 together with an identification of the head and body structure of the fetus may be used to determine whether there is a placental structure over the cervix per condition (i). Gestational age may be computed according to the fetal size measurements in light of whether there are multiple gestations completing the measurements of process block 106. These conditions may then be output as described above with respect to process block 82 of FIG. 3

Segmentation techniques for fetal measurement are described generally in U.S. Pat. No. 8,556,814 "Automated fetal measurement from three-dimensional ultrasound data"; U.S. Pat. No. 7,995,820 "System and method for detection of fetal anatomies from ultrasound images using a constrained probabilistic boosting tree"; U.S. Pat. No. 7,783, 095 "System and method for fetal biometric measurements from ultrasound data and fusion of same for estimation of fetal gestational age"; and U.S. Pat. No. 7,400,767 "System and method for graph cuts image segmentation using a shape prior"; all hereby incorporated by reference.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. A medical ultrasound machine comprising:
   an ultrasound transducer assembly including:
   a transducer bar adapted to be supported by a hand of a human, wherein the transducer bar includes a set of independently excitable transducer elements extending along a lateral axis of the transducer bar and the set of independently excitable transducer elements are exposed for ultrasonic transmission and reception; and
   an ultrasound processor assembly including:
   (1) transducer interface circuitry communicating with the set of independently excitable transducer elements for acquisition of slices of ultrasound echo data to complete a volume set of ultrasound echo signals;
   (2) a display; and
   (3) an electronic processor receiving the slices of ultrasound echo data to complete the volume set of ultrasound echo signals and executing a stored program to identify within the completed volume set of ultrasound echo signals indications of conditions selected from the group of:
   (i) placenta over cervix;
   (ii) fetus in non-head down presentation;
   (iii) multiple gestation;
   (iv) gestational age; and
   (v) fetal size;
   and to output at least one of the conditions on the display;
   wherein the electronic processor further outputs on the display at least one of a shading and/or a trajectory guiding movement of the ultrasound transducer assembly to obtain the volume set of ultrasound echo signals; and
   wherein the shading and/or trajectory guiding movement of the ultrasound transducer assembly is based on concurrent analysis of previously received slices of ultrasound data from preceding ultrasound transducer assembly positions by the electronic processor to assemble a partial volume of ultrasound data from the previously received slices and analyze the partial volume to determine slices of ultrasound data still needed to complete the volume set of ultrasound echo signals.

2. The medical ultrasound machine of claim 1 further comprising a hand retention element extendable upward from the transducer bar to retain the transducer bar against the hand wherein the hand retention element and transducer bar are substantially symmetric across a plane perpendicular to the lateral axis to receive either a left or right hand.

3. The medical ultrasound machine of claim 1 wherein the ultrasound transducer assembly includes indicia indicating preferred movement direction.

4. The medical ultrasound machine of claim 1 wherein the electronic processor further executes the stored program to output the at least one condition independent of a representation of an image of the volume set of ultrasound echo signals.

5. The medical ultrasound machine of claim 4 wherein the electronic processor executes the stored program to output the at least one condition without outputting a representation of an image of the volume set of ultrasound echo signals.

6. The medical ultrasound machine of claim 1 wherein the electronic processor executes the stored program to output on the display an output free from information identifying gender.

7. The medical ultrasound machine of claim 1 wherein real-time analysis of the electronic processor analyzes the received ultrasound signals to identify fetal structure and wherein the shading and/or trajectory guiding movement of the ultrasound transducer assemble are based on identified fetal structure that must be measured for identification of the at least one condition.

8. The medical ultrasound machine of claim 1 wherein the shading and/or trajectory guiding movement of the ultrasound transducer assembly provide a representation of the ultrasound transducer assembly positioned on a representation of a mother's abdomen.

9. The medical ultrasound machine of claim 1 wherein the least one condition includes the placenta over cervix.

10. The medical ultrasound machine of claim 1 wherein the least one condition includes the fetus in non-head down presentation.

11. The medical ultrasound machine of claim 1 wherein the least one condition includes the multiple gestation.

12. The medical ultrasound machine of claim 1 wherein the least one condition includes the gestational age.

13. The medical ultrasound machine of claim 1 wherein the least one condition includes the fetal size.

14. The medical ultrasound machine of claim 1 wherein the electronic processor executes a stored program to display an indication of a received volume set independent of a representation of an image of the volume set of ultrasound echo signals.

15. The medical ultrasound machine of claim 14 wherein the indication of the acquired slices of ultrasound echo data is a progressively shaded predetermined representation of the patient's abdominal area.

16. The medical ultrasound machine of claim 2 wherein the hand retention element provides an internal cavity.

17. The medical ultrasound machine of claim 1 wherein the transducer bar has an upper surface receivable against a palm of a hand placed thereagainst to extend across the lateral axis and further comprising a hand retention element extendable upward from the transducer bar to retain the transducer bar against the palm.

18. The medical ultrasound machine of claim 17 wherein the transducer bar supports the set of independently excitable transducer element at a lower surface of the transducer bar opposite the upper surface.

19. The medical ultrasound machine of claim 8 wherein the representation of the mother's abdomen is a cartoon.

20. The medical ultrasound machine of claim 1 wherein overlapping slices of ultrasound echo data are stitched together to form the volume set of ultrasound echo signals.

21. The medical ultrasound machine of claim 1 wherein the electronic processor is configured to analyze the partial volume to determine a superior/inferior axis of a patient's abdomen.

22. The medical ultrasound machine of claim 21 wherein analyzing the partial volume to determine the superior/ inferior axis of the patient's abdomen is based on an order of acquisition of the previously received slices forming the partial volume.

23. The medical ultrasound machine of claim 1 wherein the electronic processor is configured to analyze the partial volume to identify anatomical structures and to use the anatomical structures as reference points to identify additional slices needed for the volume set.

24. The medical ultrasound machine of claim 1 wherein the slices are assembled into a partial volume by correlating features of the slices.

25. A method of performing an ultrasonic evaluation of an expectant mother using a medical ultrasound machine having:
   an ultrasound transducer assembly including:
   a transducer bar having a set of independently excitable transducer elements extending along a lateral axis of the transducer bar and exposed for ultrasonic transmission and reception; and
   an ultrasound processor assembly including:
   (1) transducer interface circuitry configured to communicate with the set of independently excitable transducer elements for acquisition of slices of ultrasound echo data to complete a volume set of ultrasound echo signals;
   (2) a display; and
   (3) an electronic processor configured to receive the slices of ultrasound echo data to complete the volume set of ultrasound echo signals and execute a stored program to identify within the completed volume set of ultrasound echo signals indications of conditions selected from the group of:
   (i) placenta over cervix;
   (ii) fetus in non-head down presentation;
   (iii) multiple gestation;
   (iv) gestational age; and
   (v) fetal size;
   the method comprising:
   outputting on the display a shading and/or a trajectory guiding movement of the ultrasound transducer assembly to obtain the volume set of ultrasonic echo signals;
   sweeping the ultrasonic transducer assembly over a patient's abdomen according to the shading and/or trajectory guiding movement of the ultrasound transducer assembly to collect the volume set of ultrasound data to provide a measure of at least one of the condition wherein the shading and/or trajectory guiding movement of the ultrasound transducer assembly is based on concurrent analysis of previously received ultrasound signals from preceding ultrasound transducer assembly positions by the electronic processor to assemble a partial volume of ultrasound data from the previously received slices and analyze the partial volume to determine the slices of ultrasound data still needed to complete the volume set of ultrasound echo signals; and
   outputting the at least one condition based on the completed volume set of ultrasound echo signals on the display.

* * * * *